United States Patent

Langer et al.

(10) Patent No.: US 6,753,444 B2
(45) Date of Patent: Jun. 22, 2004

(54) METHOD FOR PRODUCING 2,3,5,6-TETRAHALOGEN-XYLYIDENE COMPOUNDS

(75) Inventors: Reinhard Langer, Tönisvorst (DE); Lars Rodefeld, Leverkusen (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 10/181,997

(22) PCT Filed: Jan. 17, 2001

(86) PCT No.: PCT/EP01/00446
§ 371 (c)(1), (2), (4) Date: Jul. 24, 2002

(87) PCT Pub. No.: WO01/55064
PCT Pub. Date: Aug. 2, 2001

(65) Prior Publication Data
US 2002/0198401 A1 Dec. 26, 2002

(30) Foreign Application Priority Data
Jan. 27, 2000 (DE) ............ 100 03 320

(51) Int. Cl.$^7$ ............ C07C 69/76; C07C 67/02; C07C 41/00; C07C 43/02; C07C 43/20
(52) U.S. Cl. ............ 560/111; 560/254; 568/660; 568/661; 568/662; 568/663; 568/811; 568/812; 570/124; 570/144; 570/185
(58) Field of Search ............ 560/111, 254; 568/660, 661, 662, 663, 811, 812; 570/124, 144, 185

(56) References Cited

U.S. PATENT DOCUMENTS 6,452,056 B1 * 9/2002 Kawanobe et al. ......... 568/700
2003/0171626 A1 * 9/2003 Murakami et al. ......... 568/811

FOREIGN PATENT DOCUMENTS

EP 0 099 622 2/1984
EP 0 152 174 8/1985
GB 2127013 4/1984

OTHER PUBLICATIONS

*Database Chemabs 'Online! Chemical Abstracts Service, Columbus, Ohio, US; Sumitomo Chemical Co., LTD., Japan: "Hydroxydiphenylamines" retrieved from STN Database accession No. 102:113026 CA XP002169098 Zusammenfassung & JP 59 206338 A (Sumitomo Chemical Co., Ltd., Japan) Nov. 22, 1984.

* cited by examiner

Primary Examiner—Richard L. Raymond
Assistant Examiner—Zachary C. Tucker
(74) Attorney, Agent, or Firm—Godfried R. Akorli; Diderico van Eyl

(57) ABSTRACT

The invention relates to a process for preparing 2,3,5,6-tetrahaloxylylidene compounds of formula (I)

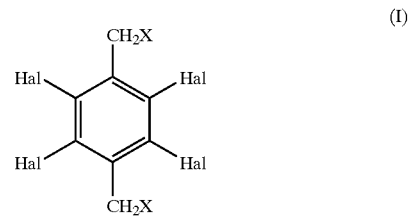

where each Hal is independently fluorine or chlorine, and X is fluorine, chlorine, bromine, —O—R, or —O—C(=O)R, where R is hydrogen, a straight-chain or branched $C_1$–$C_{12}$-alkyl- or a $C_6$–$C_{14}$-aryl radical, by reacting 2,3,5,6-tetrahaloxylylidenediamines of formula (II)

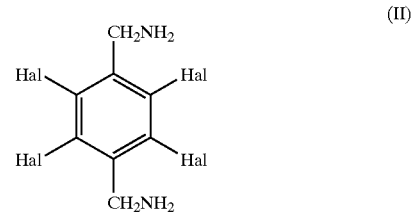

with an alkyl nitrite and/or nitrous acid in HX as a solvent.

15 Claims, No Drawings

METHOD FOR PRODUCING 2,3,5,6-TETRAHALOGEN-XYLYIDENE COMPOUNDS

The present invention relates to the preparation of 2,3,5,6-tetrahaloxylylidene compounds by diazotization of 2,3,5,6-tetrahaloxylylidenediamine.

2,3,5,6-Tetrahaloxylylidene compounds are known to those skilled in the art as important intermediates, for example for preparing active pharmaceutical or agrochemical ingredients such as insecticides.

The preparation of 2,3,5,6-tetrahaloxylylidenediols, their esters and ethers is only possible by few prior art methods: for example, GB-A-21 27 013 describes the reduction of tetrafluoroterephthalyl chloride using sodium borohydride to give tetrafluoroxylylidenediol and also the subsequent esterification using acetyl chloride to give tetrafluoroterephthalyl acetate.

EP-A-0 152 174 further discloses a complicated reaction sequence starting from 2,3,5,6-tetrafluorotoluene which involves metallation, methylation, bromination, substitution of the xylylidene dibromide by potassium acetate and hydrolysis to give 2,3,5,6-tetrahaloxylylidenediol.

The preparation of tetrahaloxylylidenediamine by hydrogenation of tetrahaloterephthalonitrile using a hydrogenation catalyst based on rhodium, palladium, ruthenium, nickel, cobalt or platinum and also in the presence of acids is described in EP-A-099 622.

The conversion of 2,3,5,6-tetrahaloxylylidenediamine to 2,3,5,6-tetrahaloxylylidene compounds with cleavage of the N—C bond has hitherto not been described.

It is an object of the present invention to provide a process which facilitates industrial preparation of 2,3,5,6-tetrahaloxylylidene compounds with high space-time yields from simple precursors.

The invention provides a process for preparing 2,3,5,6-tetrahaloxylylidene compounds of the general formula (I)

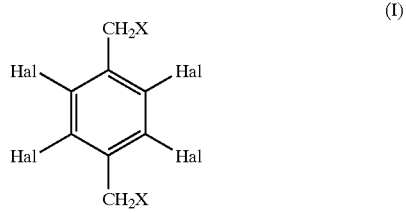

(I)

where each Hal, which may be the same or different, is fluorine or chlorine and X is fluorine, chlorine, bromine, —O—R or —O—C(=O)R, where R is hydrogen, a straight-chain or branched $C_1$–$C_{12}$-alkyl- or a $C_6$–$C_{14}$-aryl radical,
by reacting 2,3,5,6-tetrahaloxylylidenediaimines of the general formula (II)

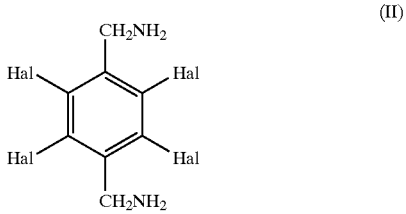

(II)

where Hal is as defined for the general formula (I),
characterized in that compounds of the general formula (II) are reacted with alkyl nitrites and/or nitrous acid in HX as a solvent, where X in HX is as defined for the general formula (I).

In the process according to the invention, the substituent X in the general formula (I) and also in HX is preferably fluorine, hydroxyl, OR or —O—C(=O)R, where R is hydrogen or a straight-chain or branched $C_1$–$C_6$, in particular a $C_1$–$C_4$-alkyl radical. More preferably, the solvent HX used is water, so that the compounds obtained of the general formula (I) are 2,3,5,6-tetrahaloxylylidenediols.

The diazotization of the 2,3,5,6-tetrahaloxylylidenediamines of the formula (II) is effected in the process according to the invention in the presence of alkyl nitrites and/or nitrous acid. Useful alkyl nitrites include $C_1$–$C_{10}$-alkyl nitrites, and isoamyl, ethyl or methyl nitrite are preferably used, and methyl nitrite is most preferably used. Instead of or in addition to the alkyl nitrite, nitrous acid may also be used. This can also be prepared in situ from an alkali metal nitrite and/or an alkaline earth metal nitrite and a mineral acid and/or a carboxylic acid. In this case, the alkali metal nitrite and/or alkaline earth metal nitrite is preferably calcium nitrite, magnesium nitrite, sodium nitrite or potassium nitrite, and the mineral acid is preferably sulfuric acid, hydrochloric acid, hydrofluoric acid, chlorosulfonic acid, fluorosulfonic acid or phosphoric acid. The carboxylic acid may, for example, be formic acid, acetic acid, propionic acid or benzoic acid.

A preferred embodiment of the process according to the invention employs, in addition to the solvent HX, one or more other inert solvents. Useful other inert solvents for the process according to the invention include $C_3$–$C_{30}$-, preferably $C_6$–$C_{12}$-alkanes, $C_5$–$C_{30}$-, preferably $C_6$–$C_{12}$-cycloalkanes, $C_6$–$C_{20}$-, preferably $C_6$–$C_{18}$-aromatics, $C_3$–$C_{30}$-esters and $C_3$–$C_{30}$-ethers. Preference is given to using hexane, heptane, petroleum ether, cyclohexane, decalin, benzene, toluene, the xylenes, chlorobenzene, dichlorobenzene, trichlorobenzene, ethyl acetate, butyl acetate, diethyl ether, tetrahydrofuran or diphenyl ether.

It will also be advantageous to adjust the pH of the reaction mixture by addition of mineral acids and/or carboxylic acids to a value of from 0 to 9, preferably from 2 to 7 and more preferably from 3 to 5. The mineral and carboxylic acids used may be the compounds already mentioned above for the in situ preparation of nitrous acid.

The process according to the invention is operated at temperatures of from 0 to 100° C., preferably from 30 to 60° C.

The pressure during the diazotization is from 0.2 to 200 bar, preferably from 0.5 to 50 bar and more preferably from 1 to 10 bar.

The molar ratio of the compounds of the formula (II) to the alkyl nitrite and/or to nitrous acid is from 1:(2–10), preferably 1:(2–4). The reaction solution has a reactant content of from 1 to 50% by weight, preferably from 5 to 25% by weight.

The process according to the invention may be operated in customary reactors, and batchwise, semicontinuously or continuously. The exact industrial embodiment depends on the process parameters and may be determined easily by those skilled in the art.

The starting materials for the process according to the invention are compounds of the formula (II), which are preferably obtained by hydrogenation of the appropriate tetrahaloterephthalonitriles.

A preferred embodiment involves operating the process according to the invention in such a way that the compounds of the formula (II) are prepared by hydrogenation of compounds of the general formula (III)

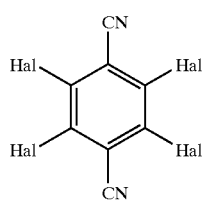

where Hal and X are as defined for the general formula (I), in the presence of a hydrogenation catalyst and a solvent HX.

Useful hydrogenation catalysts include all customary and known catalysts for the hydrogenation of nitrites. In particular, catalysts based on elements of transition group VIII of the periodic table have proven useful. Preference is given to using hydrogenation catalysts based on rhodium, palladium, ruthenium, nickel, cobalt or platinum, and particular preference to using palladium catalysts.

Hydrogenation is also carried out in the presence of one or more solvents HX, where X is as defined for the formula (I). Other inert solvents may optionally also be present. The reaction temperature of the hydrogenation is from −30 to +60° C., preferably from 0 to 30° C., and the pressure from 3 to 300 bar, preferably from 10 to 100 bar. Preference is given to hydrogenating in the presence of mineral acids and/or carboxylic acids. The mineral acids and carboxylic acids used may be those already mentioned for the process according to the invention.

A particularly advantageous process variant is characterized by the compound of the formula (II) obtained by hydrogenation being freed from the hydrogenation catalyst by filtration and, if necessary after distillative removal of troublesome solvent, introduced directly to the diazotization without an intervening isolation. This may be carried out by using the reaction solution obtained after hydrogenation as an initial charge and adding the diazotizing reagent alkyl nitrite and/or nitrous acid, or vice versa.

The process according to the invention delivers the desired 2,3,5,6-tetrahaloxylylidene compounds in high purity and with high space-time yield via simple process steps.

EXAMPLES

Example 1
Preparation of 2,3,5,6-tetrafluoroxylylidenediamine as a Sulfuric Acid Solution
1 249.5 g (6.24 mol) of 2,3,5,6-tetrafluoroterephthalonitrile are initially charged to a 10 l autoclave together with 750 ml of methanol, 5 250 ml of water, 1 050 g of concentrated sulfuric acid and 75 g of a 5% palladium-carbon catalyst and hydrogenated at 30° C. and 30 bar of hydrogen pressure until constant pressure is obtained. The catalyst is filtered off. The methanol is then distilled off again at 80 to 90° C. and 350 mbar. 6 690 g of a sulfuric acid solution are obtained, which according to GC analysis (external standard) contains 1 197.2 g (5.75 mol) of tetrafluoroxylylidenediamine (92% yield).

Example 2
Preparation of 2,3,5,6-tetrafluoroxylylidenediol
3 200 g (2.87 mol of compound) of a tetrafluoroxylylidenediamine hydrosulfate solution prepared as above are adjusted to pH 4 using 868 g of 20% sodium hydroxide solution. The reaction mixture is heated to 80 to 90° C. and 981 g of a 40% sodium nitrite solution are added dropwise within 4 h. Simultaneously, the pH of the solution is held between 3 and 5 with the aid of 127 g of 30% sulfuric acid. When no more gas is formed, the reaction batch is extracted twice with 750 ml of ethyl acetate and the organic phase is then concentrated under reduced pressure. 456 g (2.17 mol) of 2,3,5,6-tetrafluoroxylylidenediol are obtained in a purity of 74.5% and a yield of 76%.

What is claimed is:
1. A process for preparing 2,3,5,6-tetrahaloxylylidene compound of formula (I)

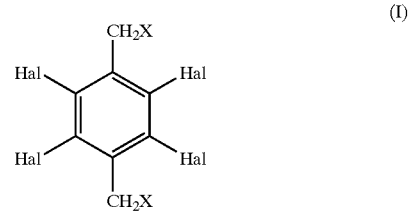

where
each Hal is independently fluorine or chlorine, and
X is fluorine, chlorine, bromine, —O—R, or —O—C(=O)R, where R is hydrogen, a straight-chain or branched $C_1$–$C_{12}$-alkyl- or a $C_6$–$C_{14}$-aryl radical,
comprising reacting a 2,3,5,6-tetrahaloxylylidenediamine of formula (II)

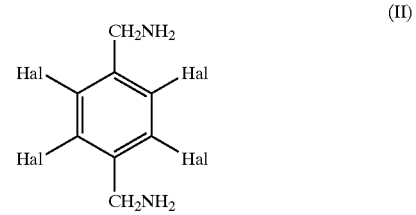

where Hal is as defined for formula (I), with an alkyl nitrite and/or nitrous acid in HX as a solvent, where X is as defined for formula (I).

2. The process as claimed in claim 1 wherein X in formula (I) or in HX is fluorine, hydroxyl, OR, or —O—C(=O)R, where R is hydrogen or $C_1$–$C_6$-alkyl.

3. The process as claimed in claim 1 wherein the alkyl nitrite is a $C_1$–$C_{10}$-alkyl nitrite.

4. The process as claimed in claim 1 wherein nitrous acid is used instead of or in addition to the alkyl nitrite.

5. The process as claimed in claim 4 wherein the nitrous acid is prepared in situ from an alkali metal nitrite and/or an alkaline earth metal nitrite and a mineral acid and/or a carboxylic acid.

6. The process as claimed in claim 5 wherein the alkali metal nitrite or alkaline earth metal nitrite is calcium nitrite, magnesium nitrite, sodium nitrite, or potassium nitrite; the mineral acid is sulfuric acid, hydrochloric acid, hydrofluoric acid, chlorosulfonic acid, fluorosulfonic acid, or phosphoric acid; and the carboxylic acid is formic acid, acetic acid, propionic acid, or benzoic acid.

7. The process as claimed in claim 1 carried out in the presence of water using HX as solvent.

8. The process as claimed in claim 1 wherein the pH of the reaction mixture is adjusted by addition of a mineral acid and/or carboxylic acid to a value of from 0 to 9.

9. The process as claimed in claim 8 wherein the mineral acid is sulfuric acid, hydrochloric acid, hydrofluoric acid, chlorosulfonic acid, fluorosulfonic acid, or phosphoric acid; and the carboxylic acid is formic acid, acetic acid, propionic acid, or benzoic acid.

10. The process as claimed in claim 1 carried out at temperatures of from 0 to 100° C. and a pressure of from 0.2 to 200 bar.

11. The process as claimed in claim 1 wherein the compound of formula (II) is obtained by hydrogenation of a compound of formula (III)

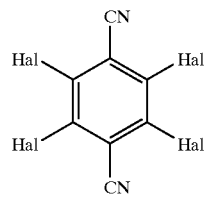

(III)

where Hal and X are as defined for formula (I), in the presence of a hydrogenation catalyst and a solvent HX.

12. The process as claimed in claim 11 wherein the hydrogenation catalyst is based on elements of transition group VIII of the periodic table.

13. The process as claimed in claim 11 wherein the hydrogenation catalyst is based on rhodium, palladium, ruthenium, nickel, cobalt or platinum.

14. The process as claimed in claim 11 carried out in the presence of one or more solvents HX, where X is as defined for formula (I), at a reaction temperature of from −30 to +60° C., and at a pressure of from 3 to 300 bar.

15. The process as claimed in claim 1 wherein the compound of formula (II) is (i) obtained by hydrogenation of a compound of formula (III)

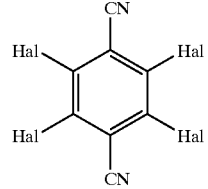

(III)

where Hal and X are as defined for formula (I), in the presence of a hydrogenation catalyst and a solvent HX, (ii) freed from the hydrogenation catalyst by filtration, optionally followed by distillative removal of the solvent, and (iii) introduced directly to the process as claimed in claim 1.

* * * * *